US010010356B2

(12) United States Patent
Schmierer et al.

(10) Patent No.: US 10,010,356 B2
(45) Date of Patent: Jul. 3, 2018

(54) BONE PLATES, SCREWS AND INSTRUMENTS

(71) Applicant: Wenzel Spine, Inc., Austin, TX (US)

(72) Inventors: Douglas E. Schmierer, Dallas, TX (US); Charles R. Forton, Frisco, TX (US); Victor Zaporojan, Addison, TX (US); Marc C. Yap, The Colony, TX (US)

(73) Assignee: Wenzel Spine, Inc., Austin, TX (US)

( * ) Notice: Subject to any disclaimer, the term of this patent is extended or adjusted under 35 U.S.C. 154(b) by 0 days.

(21) Appl. No.: 15/284,303

(22) Filed: Oct. 3, 2016

(65) Prior Publication Data

US 2017/0020587 A1   Jan. 26, 2017

Related U.S. Application Data

(63) Continuation of application No. 14/569,191, filed on Dec. 12, 2014, now Pat. No. 9,456,858, which is a
(Continued)

(51) Int. Cl.
*A61B 17/80*   (2006.01)
*A61B 17/16*   (2006.01)
(Continued)

(52) U.S. Cl.
CPC ...... *A61B 17/8033* (2013.01); *A61B 17/1659* (2013.01); *A61B 17/1671* (2013.01);
(Continued)

(58) Field of Classification Search
CPC ............ A61B 17/8033; A61B 17/1659; A61B 17/1671; A61B 17/7007; A61B 17/7059; A61B 17/7062; A61B 17/7064; A61B 17/7068; A61B 17/8047; A61B 17/809; A61B 17/8028; A61B 50/30
(Continued)

(56) References Cited

U.S. PATENT DOCUMENTS 3,242,922 A   3/1966   Thomas
3,469,573 A   9/1969   Florio
(Continued)

FOREIGN PATENT DOCUMENTS

EP   1477124 B1   10/2007
JP   2004-535239 A   11/2004
(Continued)

OTHER PUBLICATIONS

"OHSU Surgeons Find New Way to Fix Painful Broken Ribs," Oregon Health & Science University, http://www.ohsu.edu.ohsuedu/newspub/releases/062706ribs.cfm, Jun. 27, 2006.
(Continued)

*Primary Examiner* — Pedro Philogene
*Assistant Examiner* — David C Comstock
(74) *Attorney, Agent, or Firm* — Baker Botts L.L.P.

(57) ABSTRACT

Systems for trauma and/or joint fusion implants and instruments include transarticular screw and intra-articular washer, polyaxial screw and plate, single- and multi-level polyaxial bone clamps, and minimally invasive adaptations.

20 Claims, 14 Drawing Sheets

Related U.S. Application Data continuation of application No. 14/154,121, filed on Jan. 13, 2014, now Pat. No. 8,911,476, which is a continuation of application No. 13/452,602, filed on Apr. 20, 2012, now Pat. No. 8,636,772, which is a continuation-in-part of application No. 13/188,325, filed on Jul. 21, 2011, now Pat. No. 8,721,686, which is a continuation-in-part of application No. 12/853,689, filed on Aug. 10, 2010, now Pat. No. 9,211,147, said application No. 12/853,689 is a continuation-in-part of application No. 12/820,575, filed on Jun. 22, 2010, now Pat. No. 8,377,097.

(60) Provisional application No. 61/366,755, filed on Jul. 22, 2010, provisional application No. 61/477,966, filed on Apr. 21, 2011, provisional application No. 61/232,692, filed on Aug. 10, 2009, provisional application No. 61/219,687, filed on Jun. 23, 2009.

(51) Int. Cl.
*A61B 17/70* (2006.01)
*A61B 50/30* (2016.01)

(52) U.S. Cl.
CPC ...... *A61B 17/7007* (2013.01); *A61B 17/7059* (2013.01); *A61B 17/7062* (2013.01); *A61B 17/7064* (2013.01); *A61B 17/7068* (2013.01); *A61B 17/809* (2013.01); *A61B 17/8047* (2013.01); *A61B 50/30* (2016.02); *A61B 17/8028* (2013.01)

(58) Field of Classification Search
USPC .............. 606/246–249, 257, 287; 623/17.11, 623/17.14, 17.15, 17.16
See application file for complete search history.

(56) References Cited

U.S. PATENT DOCUMENTS

| | | |
|---|---|---|
| 3,648,691 A | 3/1972 | Lumb et al. |
| 4,066,082 A | 1/1978 | Arcan et al. |
| 4,290,328 A | 9/1981 | Clark |
| D281,814 S | 12/1985 | Pratt et al. |
| 4,570,623 A | 2/1986 | Ellison et al. |
| 4,592,346 A | 6/1986 | Jurgutis |
| 4,848,328 A | 7/1989 | Laboureau et al. |
| 4,852,558 A | 8/1989 | Outerbride |
| 4,913,144 A | 4/1990 | Del Medico |
| 4,994,073 A | 2/1991 | Green |
| 5,007,909 A | 4/1991 | Rogozinski |
| 5,011,484 A | 4/1991 | Beard |
| 5,053,038 A | 10/1991 | Sheehan |
| 5,074,864 A | 12/1991 | Cozad et al. |
| 5,108,422 A | 4/1992 | Green et al. |
| 5,196,318 A | 3/1993 | Baldwin et al. |
| 5,201,746 A | 4/1993 | Shichman |
| 5,246,442 A | 9/1993 | Ashman et al. |
| 5,261,909 A | 11/1993 | Sutterlin et al. |
| 5,290,312 A | 3/1994 | Kojimoto et al. |
| 5,395,370 A | 3/1995 | Muller et al. |
| 5,454,814 A | 10/1995 | Comte |
| 5,496,318 A | 3/1996 | Howland et al. |
| 5,520,690 A * | 5/1996 | Errico ............... A61B 17/7037 606/287 |
| 5,609,634 A | 3/1997 | Voydeville |
| 5,611,800 A | 3/1997 | Davis et al. |
| 5,626,592 A | 5/1997 | Phillips et al. |
| 5,645,599 A | 7/1997 | Samani |
| 5,713,911 A | 2/1998 | Racenet et al. |
| 5,722,976 A | 3/1998 | Brown |
| 5,836,948 A | 11/1998 | Zucherman et al. |
| 5,853,414 A | 12/1998 | Groiso |
| 5,893,889 A | 4/1999 | Harrington |
| 5,941,881 A | 8/1999 | Barnes |
| 6,007,538 A | 12/1999 | Levin |
| 6,148,696 A | 11/2000 | Chiang |
| 6,238,397 B1 | 5/2001 | Zucherman et al. |
| 6,312,431 B1 | 11/2001 | Asfora |
| 6,332,883 B1 | 12/2001 | Zucherman et al. |
| 6,336,928 B1 | 1/2002 | Guerin et al. |
| 6,352,537 B1 | 3/2002 | Strnad |
| 6,364,883 B1 | 4/2002 | Santilli |
| 6,375,683 B1 | 4/2002 | Crozet et al. |
| 6,379,355 B1 | 4/2002 | Zucherman et al. |
| 6,440,169 B1 | 8/2002 | Elberg et al. |
| 6,443,987 B1 | 9/2002 | Bryan |
| 6,451,019 B1 | 9/2002 | Zucherman et al. |
| 6,485,518 B1 | 11/2002 | Cornwall et al. |
| 6,558,387 B2 | 5/2003 | Errico et al. |
| 6,565,573 B1 | 5/2003 | Ferrante et al. |
| 6,582,435 B2 | 6/2003 | Wellisz et al. |
| 6,641,585 B2 | 11/2003 | Sato et al. |
| 6,695,842 B2 | 2/2004 | Zucherman et al. |
| 6,699,247 B2 | 3/2004 | Zucherman et al. |
| 6,712,819 B2 | 3/2004 | Zucherman et al. |
| 6,761,720 B1 | 7/2004 | Senegas |
| 6,783,531 B2 | 8/2004 | Allen |
| 6,796,983 B1 | 9/2004 | Zucherman et al. |
| 6,923,812 B1 | 8/2005 | Wellisz |
| 6,969,391 B1 | 11/2005 | Gazzani |
| 7,025,787 B2 | 4/2006 | Bryan et al. |
| 7,048,736 B2 | 5/2006 | Robinson et al. |
| 7,060,068 B2 | 6/2006 | Tromanhauser et al. |
| 7,229,444 B2 | 6/2007 | Boyd |
| 7,250,060 B2 | 7/2007 | Trieu |
| 7,255,698 B2 | 8/2007 | Michelson |
| 7,294,128 B2 | 11/2007 | Alleyne et al. |
| 7,335,203 B2 | 2/2008 | Winslow et al. |
| 7,377,921 B2 | 5/2008 | Studer et al. |
| 7,393,361 B2 | 7/2008 | Zubok et al. |
| 7,396,360 B2 | 7/2008 | Lieberman |
| 7,588,592 B2 | 9/2009 | Winslow et al. |
| 7,666,228 B2 | 2/2010 | Le Couedic et al. |
| 7,727,233 B2 | 6/2010 | Blackwell et al. |
| 7,857,857 B2 | 12/2010 | Kim |
| 7,862,592 B2 | 1/2011 | Peterson et al. |
| 7,871,426 B2 | 1/2011 | Chin et al. |
| 7,935,133 B2 | 5/2011 | Malek |
| 7,955,392 B2 | 6/2011 | Dewey et al. |
| 8,043,337 B2 | 10/2011 | Klyce et al. |
| 8,048,120 B1 | 11/2011 | Fallin et al. |
| 8,070,817 B2 | 12/2011 | Gradl et al. |
| 8,114,132 B2 | 2/2012 | Lyons et al. |
| 8,128,659 B2 | 3/2012 | Ginsberg et al. |
| 8,157,842 B2 | 4/2012 | Phan et al. |
| 8,636,772 B2 | 1/2014 | Schmierer et al. |
| 8,911,476 B2 | 12/2014 | Schmierer et al. |
| 2001/0020188 A1 | 9/2001 | Sander |
| 2001/0021852 A1 | 9/2001 | Chappius |
| 2003/0040746 A1 | 2/2003 | Mitchell et al. |
| 2003/0045877 A1 | 3/2003 | Yeh |
| 2003/0216736 A1 | 11/2003 | Robinson et al. |
| 2004/0034430 A1 | 2/2004 | Falahee |
| 2004/0106995 A1 | 6/2004 | Le Couedic et al. |
| 2004/0193272 A1 | 9/2004 | Zubok et al. |
| 2005/0043732 A1 | 2/2005 | Dalton |
| 2005/0137594 A1 | 6/2005 | Doubler et al. |
| 2005/0216017 A1 | 9/2005 | Fielding et al. |
| 2005/0234459 A1 | 10/2005 | Falahee et al. |
| 2005/0256582 A1 | 11/2005 | Ferree |
| 2006/0004367 A1 | 1/2006 | Alamin et al. |
| 2006/0074425 A1 | 4/2006 | Sutterlin et al. |
| 2006/0142771 A1 | 6/2006 | Beutter |
| 2006/0235391 A1 | 10/2006 | Sutterlin |
| 2006/0235518 A1 | 10/2006 | Blain |
| 2006/0241601 A1 | 10/2006 | Trautwein et al. |
| 2006/0247623 A1 | 11/2006 | Anderson et al. |
| 2006/0247634 A1 | 11/2006 | Warner et al. |
| 2006/0247640 A1 | 11/2006 | Blackwell et al. |
| 2006/0287654 A1 | 12/2006 | Posnick |
| 2007/0016189 A1 | 1/2007 | Lake et al. |
| 2007/0093823 A1 | 4/2007 | Booth et al. |

(56) References Cited

U.S. PATENT DOCUMENTS

| | | |
|---|---|---|
| 2007/0162001 A1 | 7/2007 | Chin et al. |
| 2007/0179500 A1 | 8/2007 | Chin et al. |
| 2007/0191844 A1 | 8/2007 | Carls et al. |
| 2007/0233082 A1 | 10/2007 | Chin et al. |
| 2007/0250065 A1 | 10/2007 | Efron et al. |
| 2007/0270812 A1 | 11/2007 | Peckham |
| 2007/0270840 A1 | 11/2007 | Chin et al. |
| 2007/0276384 A1 | 11/2007 | Spratt |
| 2007/0276500 A1 | 11/2007 | Zucherman et al. |
| 2008/0021471 A1 | 1/2008 | Winslow et al. |
| 2008/0021472 A1 | 1/2008 | Winslow et al. |
| 2008/0103512 A1 | 5/2008 | Gately |
| 2008/0140125 A1 | 6/2008 | Mitchell et al. |
| 2008/0147190 A1 | 6/2008 | Dewey et al. |
| 2008/0177330 A1 | 7/2008 | Ralph et al. |
| 2008/0183211 A1 | 7/2008 | Lamborne et al. |
| 2008/0183218 A1 | 7/2008 | Mueller et al. |
| 2008/0228225 A1 | 9/2008 | Trautwein et al. |
| 2008/0243185 A1 | 10/2008 | Felix et al. |
| 2008/0243186 A1 | 10/2008 | Abdou |
| 2008/0269804 A1 | 10/2008 | Holt |
| 2008/0281359 A1 | 11/2008 | Abdou |
| 2009/0018658 A1 | 1/2009 | Garcia |
| 2009/0062918 A1 | 3/2009 | Wang et al. |
| 2009/0216272 A1 | 8/2009 | Currier et al. |
| 2009/0216273 A1 | 8/2009 | Cox |
| 2009/0264927 A1 | 10/2009 | Ginsberg et al. |
| 2009/0270918 A1 | 10/2009 | Attia et al. |
| 2009/0318968 A1* | 12/2009 | Duggal .............. A61B 17/7026 606/250 |
| 2009/0326589 A1 | 12/2009 | Lemoine et al. |
| 2010/0036419 A1 | 2/2010 | Patel et al. |
| 2010/0087860 A1 | 4/2010 | Chin et al. |
| 2010/0241167 A1 | 9/2010 | Taber et al. |
| 2010/0318127 A1 | 12/2010 | Phan et al. |
| 2011/0029020 A1 | 2/2011 | Gordon et al. |
| 2011/0054531 A1 | 3/2011 | Lamborne et al. |
| 2011/0066186 A1 | 3/2011 | Boyer, II et al. |
| 2011/0144692 A1 | 6/2011 | Saladin et al. |
| 2011/0166600 A1 | 7/2011 | Lamborne et al. |
| 2011/0182693 A1* | 7/2011 | Helgerson .......... A61B 17/7064 411/337 |
| 2011/0224731 A1 | 9/2011 | Smisson, III et al. |
| 2011/0224740 A1 | 9/2011 | Smisson, III et al. |
| 2011/0313458 A1 | 12/2011 | Butler et al. |
| 2011/0319936 A1 | 12/2011 | Gordon et al. |
| 2012/0010662 A1 | 1/2012 | O'Neil et al. |
| 2012/0016418 A1 | 1/2012 | Chin et al. |
| 2012/0078304 A1 | 3/2012 | Jensen et al. |
| 2012/0078305 A1 | 3/2012 | Wang et al. |
| 2012/0083844 A1 | 4/2012 | Linares |
| 2012/0083846 A1 | 4/2012 | Wallenstein et al. |
| 2012/0089184 A1 | 4/2012 | Yeh |
| 2012/0095512 A1 | 4/2012 | Nihalani |
| 2012/0101528 A1 | 4/2012 | Souza et al. |
| 2012/0109198 A1 | 5/2012 | Dryer et al. |
| 2012/0109203 A1 | 5/2012 | Dryer et al. |
| 2012/0109205 A1 | 5/2012 | Mitchell et al. |
| 2012/0123475 A1 | 5/2012 | Ahn et al. |
| 2012/0136390 A1 | 5/2012 | Butler et al. |
| 2012/0143252 A1 | 6/2012 | Robinson |
| 2012/0150228 A1 | 6/2012 | Zappacosta et al. |
| 2012/0158061 A1 | 6/2012 | Koch et al. |
| 2012/0158063 A1 | 6/2012 | Altarac et al. |
| 2012/0310292 A1 | 12/2012 | Smisson, III et al. |

FOREIGN PATENT DOCUMENTS

| | | |
|---|---|---|
| WO | WO-00/62693 A1 | 10/2000 |
| WO | WO-03/007829 A1 | 1/2003 |
| WO | WO-2007/070819 A2 | 6/2007 |
| WO | WO-2007/109402 A2 | 9/2007 |
| WO | WO-2009/086397 A2 | 7/2009 |

OTHER PUBLICATIONS

Bostman et al., "Posterior Spinal Fusion Using Internal Fixation with the Daab Plate," Acta. Orthop. Scand., vol. 55, pp. 310-314, 1984.

Examination Report issued for Australian Patent Application No. 2010282649, dated Nov. 27, 2014, 4 pages.

Globus Medical; "SP-Fix Spinous Process Fixation Plate: Surgical Technique," pp. 1-32 Jan. 2011.

International Search Report and Written Opinion issued in International Application No. PCT/US08/88204, dated Feb. 12, 2009.

International Search Report and Written Opinion issued in international Application No. PCT/US2008/088196, dated Apr. 23, 2009.

LANX, "Aspen Spinous Process System Product Brochure," www.lanx.com, Dec. 16, 2008.

LANX, "Aspen Spinous Process System," http://www.spineansi.com/080607_Aspen_Lab_Presentation.ppt, last accessed Jun. 10, 1999.

Office Action issued for Japanese Patent Applicaiton No. 2012-189058, dated Jun. 3, 2014, 6 pages with English langugae translation.

Office Action issued for Japanese Patent Applicaiton No. 2012-524787, dated May 13, 2014, 4 pages (with English language translation).

Saint John's Health Center, "Saint John's Spine Surgeion Uses ILIF Procedure to Treat Lumbar Spinal Stenosis," www.medicalnewstoday.com/articles/155013.php.

Sénégas, "Minimally Invasive Dynamic Stabilisation of the Lumbar Motion Segment with an Interspinous Implant," Minimally Invasive Spine Surgery, pp. 459-465, 2006.

U.S. Appl. No. 60/724,632 entitled "Inter-spinous Orthopedic Device Placement and Method of Use," filed Oct. 7, 2005.

\* cited by examiner

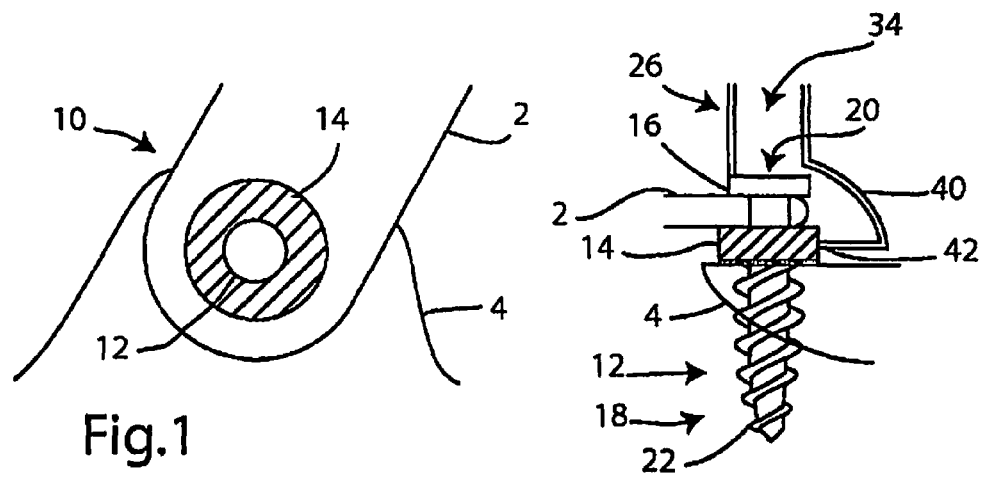
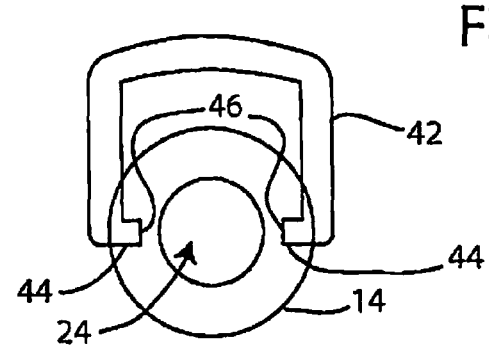
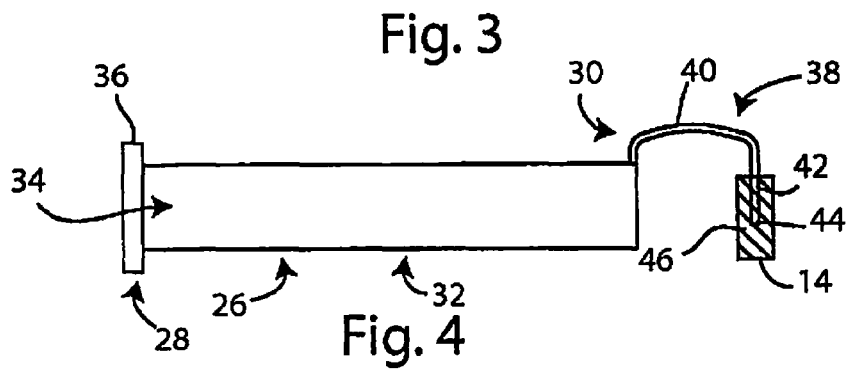
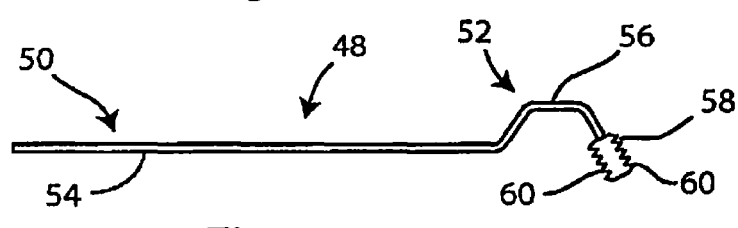

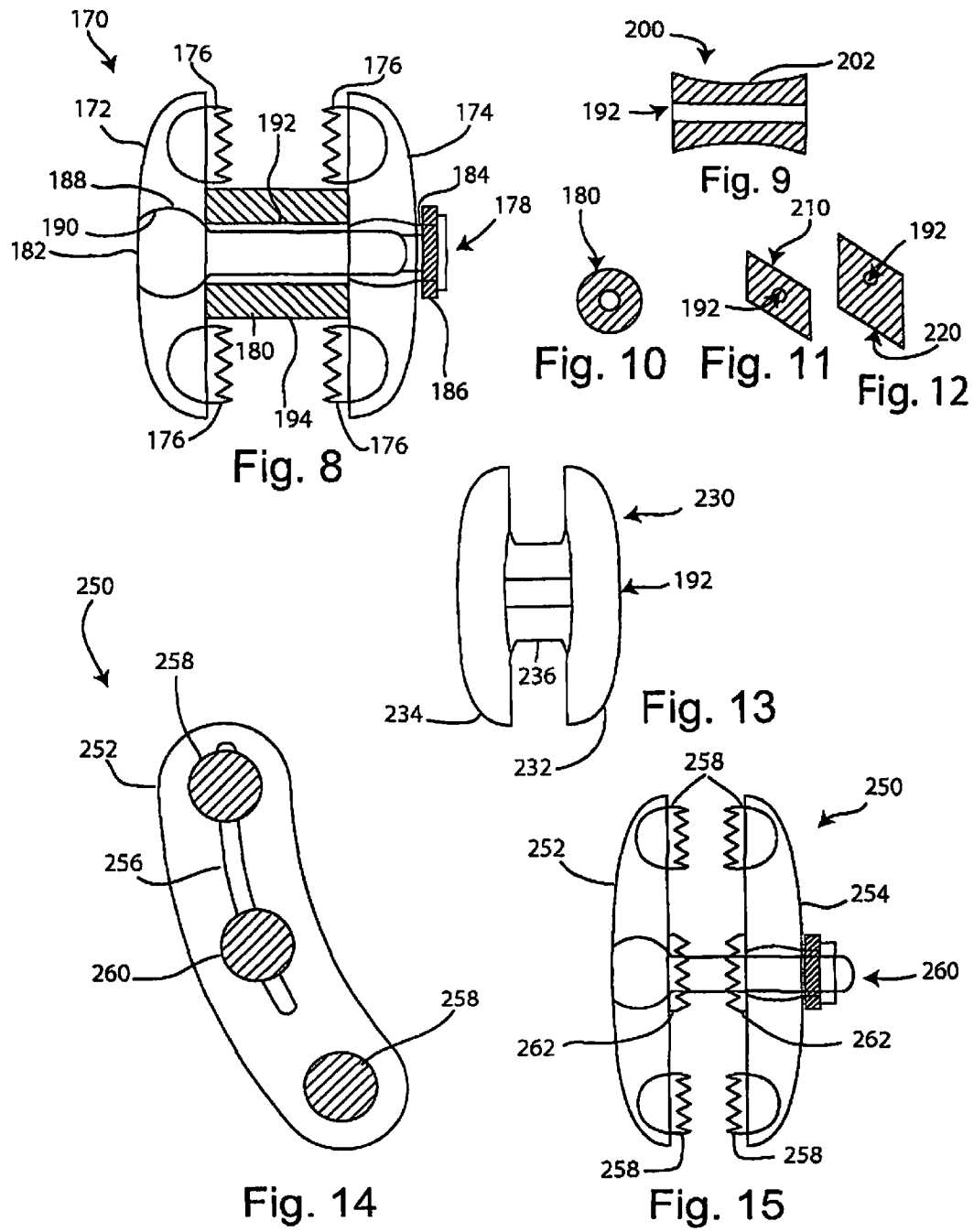

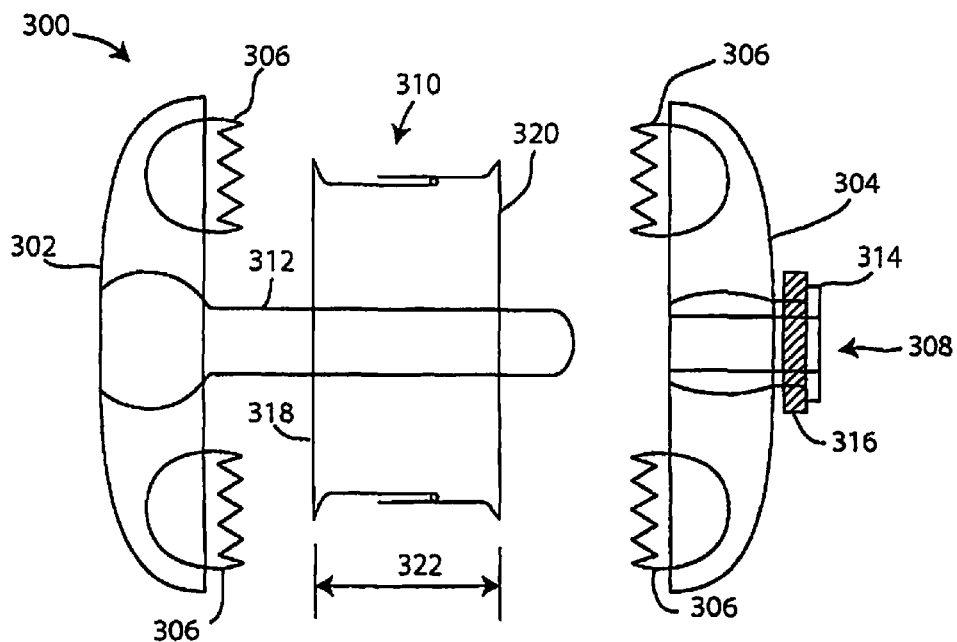
Fig. 18
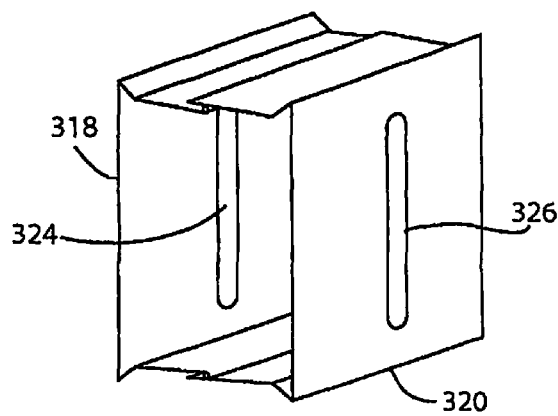
Fig. 19
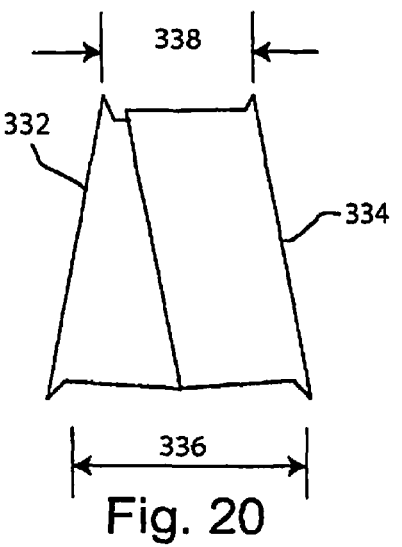
Fig. 20
Fig. 21

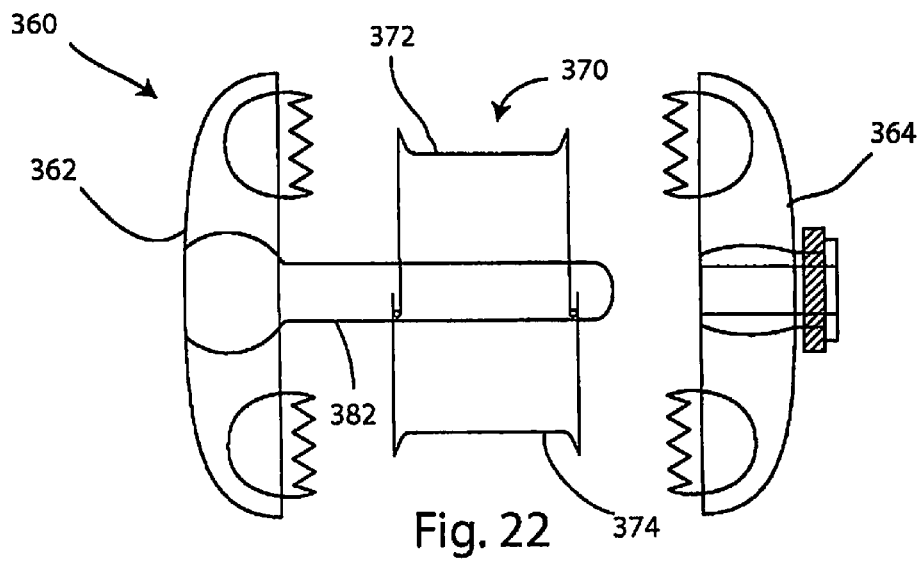
Fig. 22
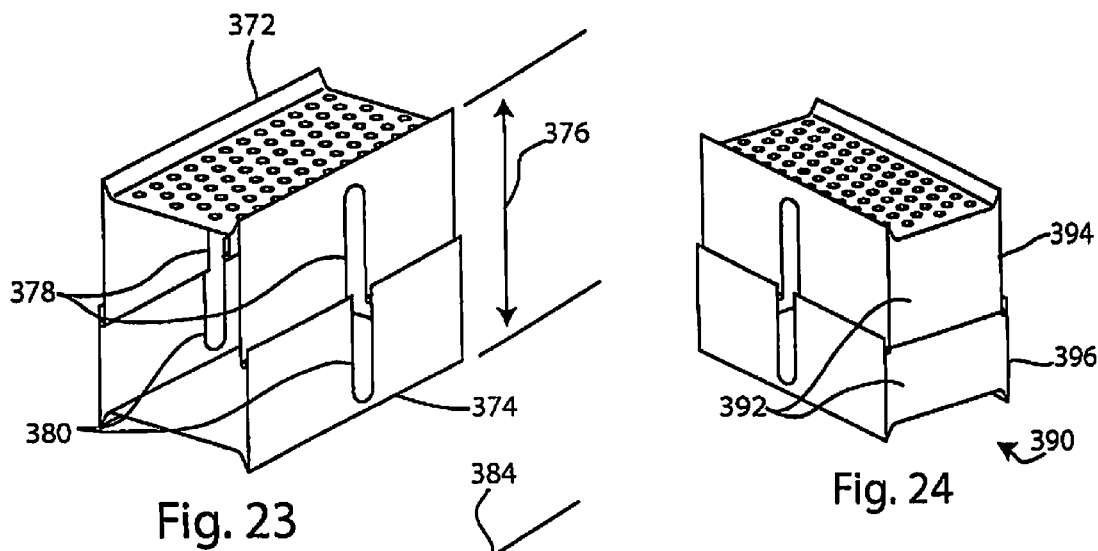
Fig. 23
Fig. 24
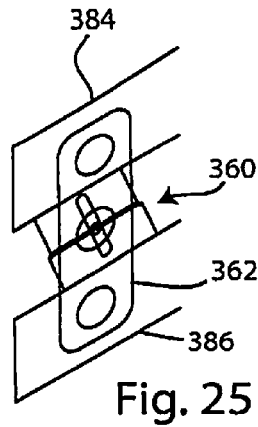
Fig. 25

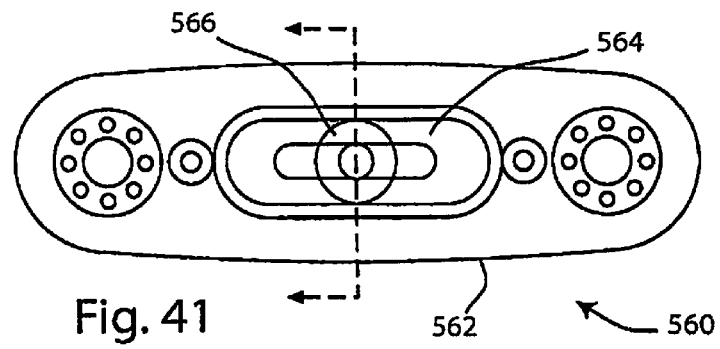
Fig. 41
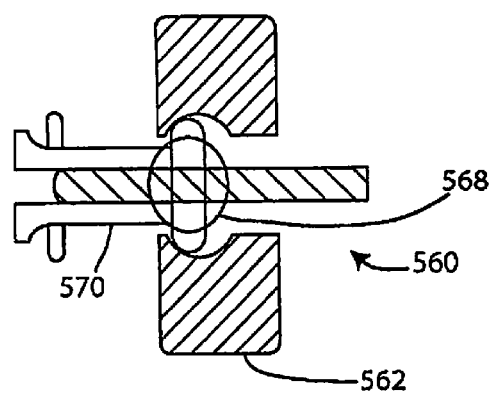
Fig. 42
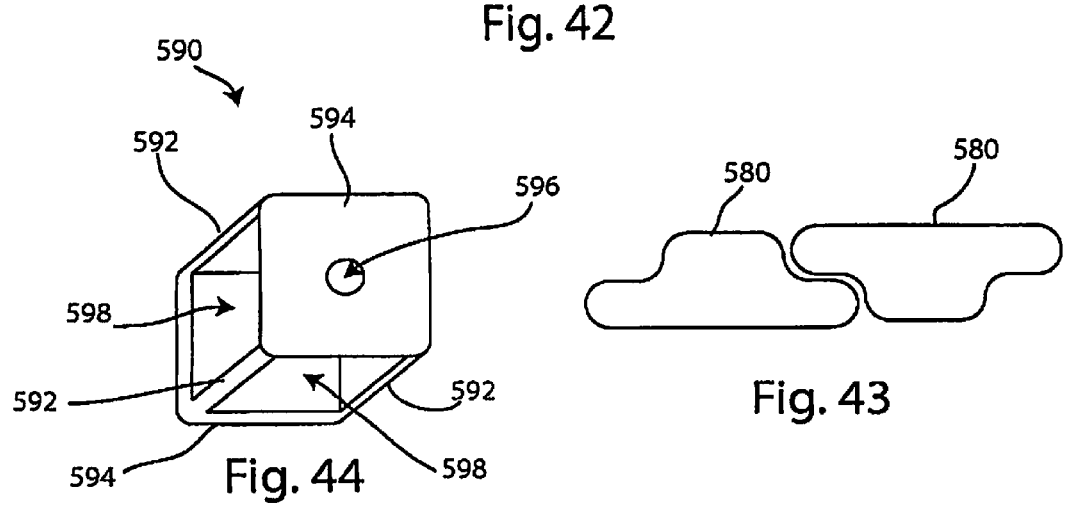
Fig. 43
Fig. 44

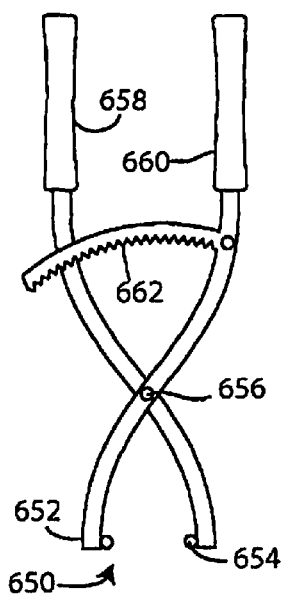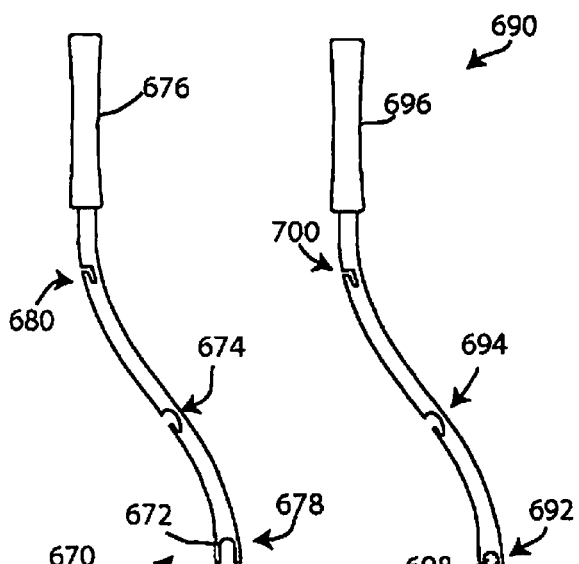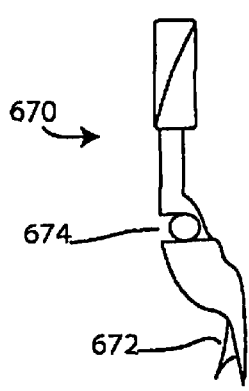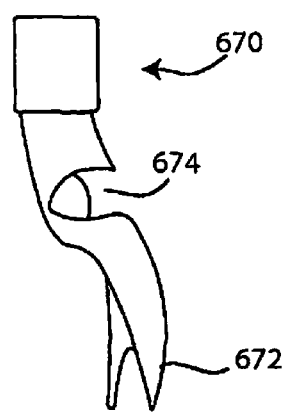
Fig. 49  Fig. 50  Fig. 51  Fig. 52  Fig. 53

BONE PLATES, SCREWS AND INSTRUMENTS

CROSS-REFERENCE TO RELATED APPLICATIONS

This application is a continuation of U.S. patent application Ser. No. 14/569,191, filed Dec. 12, 2014 and entitled, "BONE PLATES, SCREWS, AND INSTRUMENTS," which is a continuation of U.S. application Ser. No. 14/154,121, filed Jan. 13, 2014 and entitled, "BONE PLATES, SCREWS, AND INSTRUMENTS," which is a continuation of U.S. application Ser. No. 13/452,602, filed Apr. 20, 2012 and entitled, "BONE PLATES, SCREWS, AND INSTRUMENTS," issued Jan. 28, 2014 as U.S. Pat. No. 8,636,772, which is a continuation-in-part of U.S. application Ser. No. 13/188,325, filed Jul. 21, 2011 and entitled, "SPINOUS PROCESS FUSION IMPLANTS AND INSERTION COMPRESSION AND LOCKING INSTRUMENTATION," issued May 13, 2014 as U.S. Pat. No. 8,721,686, which is a continuation-in-part of U.S. application Ser. No. 12/853,689, filed Aug. 10, 2010 and entitled "SPINOUS PROCESS FUSION IMPLANTS," which is a continuation-in-part of U.S. application Ser. No. 12/820,575, filed Jun. 22, 2010 and entitled "BONE TISSUE CLAMP," issued Feb. 19, 2013 as U.S. Pat. No. 8,377,097. U.S. application Ser. No. 13/188,325 claims priority from U.S. Provisional Application No. 61/366,755, filed Jul. 22, 2010 and entitled "INSERTION, COMPRESSION AND LOCKING INSTRUMENTATION," and U.S. Provisional Application No. 61/477,966, filed Apr. 21, 2011 and entitled "BONE PLATE, SCREW, AND INSTRUMENT." U.S. application Ser. No. 12/853,689 claims priority from 61/232,692, filed Aug. 10, 2009 and entitled "SPINOUS PROCESS FUSION IMPLANTS," and U.S. Provisional Application No. 61/366,755, filed Jul. 22, 2010 and entitled "INSERTION, COMPRESSION AND LOCKING INSTRUMENTATION." U.S. application Ser. No. 12/820,575 claims priority from U.S. Provisional Application No. 61/219,687, filed Jun. 23, 2009 and entitled "BONE TISSUE CLAMP." The disclosures of all the aforementioned applications are incorporated by reference herein in their entirety.

The following document is incorporated herein by reference:

U.S. patent application Ser. No. 12/957,056, filed Nov. 30, 2010, entitled POLYAXIAL FACET FIXATION SCREW SYSTEM.

BACKGROUND

The present disclosure relates to bone plates, screws and other fasteners, and related instruments. Examples include a screw and washer system with instruments, polyaxial screw and plate systems, bone clamp systems with spacers, sleeves, and/or cages, multi-level bone clamp systems, minimally invasive bone clamp systems, motion preserving systems, and instruments for handling plates, applying compression, and applying locking forces. More specifically, the present disclosure is set forth in the context of spinal surgery, such as spine fusion or motion preservation.

BRIEF DESCRIPTION OF THE DRAWINGS

Various embodiments of the disclosed technology will now be discussed with reference to the appended drawings. It is appreciated that these drawings depict only typical embodiments of the invention and are therefore not to be considered limiting of its scope.

FIG. 1 is a transverse cross sectional view of a facet washer fixation system implanted in a facet joint, taken parallel to articular surfaces of the facet joint;

FIG. 2 is a longitudinal cross sectional view of the facet washer fixation system and facet joint of FIG. 1, taken along a center longitudinal axis of a screw of the system;

FIG. 3 is an end view of a washer of the system of FIG. 1 with a portion of a cannula;

FIG. 4 is a side view of the washer and cannula of FIG. 3;

FIG. 5 is a side view of a rasp;

FIG. 8 is a top cross sectional view of a modular spinous process clamp system;

FIG. 9 is a longitudinal cross sectional view of a sleeve for use with the system of FIG. 8;

FIG. 10 is a transverse cross sectional view of the sleeve of FIG. 9;

FIG. 11 is a transverse cross sectional view of another sleeve for use with the system of FIG. 8;

FIG. 12 is a transverse cross sectional view of yet another sleeve for use with the system of FIG. 8;

FIG. 13 is a transverse cross sectional view of yet another sleeve for use with the system of FIG. 8;

FIG. 14 is a side cross sectional view of another spinous process clamp system;

FIG. 15 is a top cross sectional view of the system of FIG. 14;

FIG. 18 is an exploded top view of yet another bone plate system;

FIG. 19 is an isometric view of a cage for use with the system of FIG. 18;

FIG. 20 is a top view of another cage for use with the system of FIG. 18;

FIG. 21 is a top view of yet another cage for use with the system of FIG. 18;

FIG. 22 is a top exploded view of yet another bone plate system;

FIG. 23 is an isometric view of a cage for use with the system of FIG. 22;

FIG. 24 is an isometric view of another cage for use with the system of FIG. 22;

FIG. 25 is a side view of the bone plate system of FIG. 22 with spinous processes;

FIG. 41 is a side view of a plate with an adjustable locking mechanism;

FIG. 42 is a transverse cross sectional view of the plate and locking mechanism of FIG. 41;

FIG. 43 is a side view of yet another segmental multi-level spinous process plating system;

FIG. 44 is an isometric view of yet another cage for use with the system of FIG. 18;

FIG. 49 is a side view of a plate compressor instrument;

FIG. 50 is a side view of a provisional locking arm for use with the compressor of FIG. 49;

FIG. 51 is a side view of a final locking arm for use with the compressor of FIG. 49;

FIG. 52 is a side view of a jaw portion of the compressor, provisional locking arm, and final locking arm of FIGS. 49-51; and FIG. 53 is another side view of the jaw portion of the compressor, provisional locking arm, and final locking arm of FIG. 52.

DETAILED DESCRIPTION OF THE PREFERRED EMBODIMENTS

Figure 6:
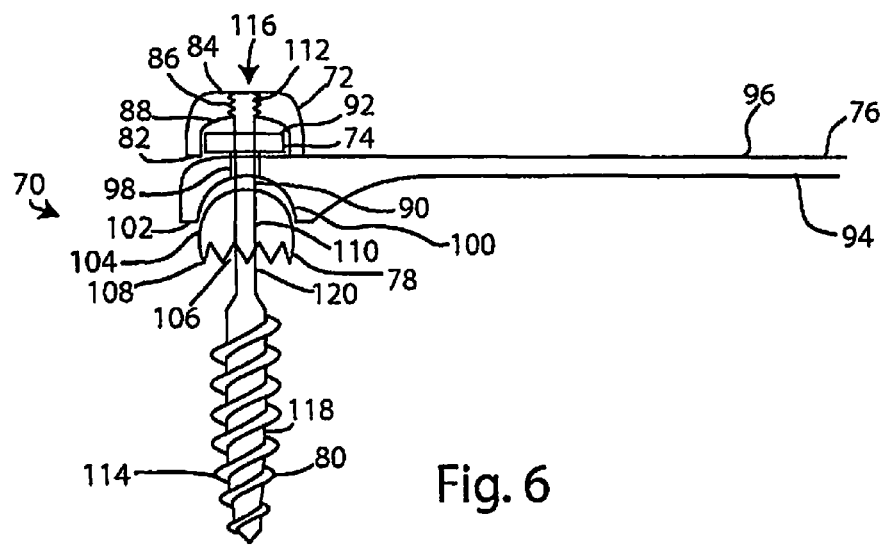
FIG. 6 is a longitudinal cross sectional view of a polyaxial taper lock screw and plate system, taken along a center longitudinal axis of a screw of the system.

The disclosed technology relates to bone plates, fasteners, and related instruments. The disclosure is made in the context of spine procedures, such as fusion or motion preservation. Those of skill in the art will recognize that the systems and methods described herein may be readily adapted to similar anatomy elsewhere in the body. Those of skill in the art will also recognize that the following description is merely illustrative of the principles of the technology, which may be applied in various ways to provide many different alternative embodiments. This description is made for the purpose of illustrating the general principles of this technology and is not meant to limit the inventive concepts in the appended claims.

Referring to FIGS. 1-2, a facet washer fixation system 10 may include a screw 12 and a washer 14.

The screw 12 may include a proximal head portion 16 and a distal shaft 18. The proximal head portion 16 may have a larger diameter than the rest of the screw 12. The proximal head portion 16 may include a torque transmission feature 20. The torque transmission feature 20 may be an internal feature, such as a straight slot, cruciform slot, square socket, hex socket, or the like. The torque transmission feature 20 may also be an external feature, such as a tab, cruciate key, square key, hex key, or the like. The distal shaft 18 may include a threaded portion 22 to thread into bone. The entire length of the shaft may be threaded, or some portion or portions thereof. The screw 12 may be similar or identical to the facet fixation screw system 10 disclosed in U.S. patent application Ser. No. 12/957,056.

The screw 12 may be made of a biocompatible material or a combination of biocompatible materials. For example, the screw 12 may be made of metal, polymer, ceramic, glass, carbon, composite, bone, or a combination of these materials.

The washer 14 may be generally annular, curved, polygonal, asymmetric, or irregular. The washer 14 may have an aperture 24 through which at least a portion of the screw 12 may pass. The distal shaft 18 of the screw 12 may pass through the aperture 24 with clearance.

The washer 14 may be made of a biocompatible material or a combination of biocompatible materials. For example, the washer 14 may be made of metal, polymer, ceramic, glass, carbon, bone, composite, or a combination of these materials. The material may stimulate bone formation on or in the washer. The material may include pores which communicate between the surface and the interior of the material. The pore morphology may be conducive to bone ingrowth.

The screw 12 may be implanted so that it passes across a joint or discontinuity between two bones or bone fragments. The washer 14 may be implanted so that it lies in the joint, or between the two bones or fragments. Some bone may extend between the screw 16 and the washer 14.

FIGS. 1-2 illustrate an arrangement in which the screw 12 and washer 14 are implanted in a facet joint of a spine. The facet joint includes an inferior articular process 2 of a superior vertebra and a superior articular process 4 of an inferior vertebra. The screw 12 is oriented generally perpendicular to the articular surfaces of the facet joint. The screw head 16 rests against the inferior articular process 2. The washer 14 is oriented generally parallel to, and between, the articular surfaces so that the inferior articular process 2 is between the screw head 16 and the washer. The inferior articular process 2 may fully encircle the distal shaft 18. The aperture 24 receives the distal shaft 18 of the screw 12.

Referring to FIGS. 2-4, the facet washer fixation system 10 may include a cannula 26. The cannula 26 may include a proximal portion 28 and a distal portion 30. The cannula 26 may also include an intermediate portion 32 which couples the proximal and distal portions 28, 30 together. The cannula 26 may be a tubular structure with a longitudinal aperture 34. The proximal portion 28 may include a grip feature 36, which may be a flange, ear, tab, handle, or the like. The grip feature 36 may be textured, such as by knurling, grooves, roughening, or by the use of a high friction material such as silicone or rubber. The distal portion 30 may carry a washer holding feature 38 which holds the washer 14 in a desired orientation and at a particular distance from the distal portion 30 of the cannula 26. The desired orientation may be influenced by the natural orientation of joint articular surfaces with respect to a selected screw trajectory. The washer holding feature 38 may include an arm 40 and a mount 42, as shown in FIGS. 2-4. The arm 40 may extend longitudinally from the distal portion 30. The arm 40 may extend from one side of the distal portion 30, and may include one or more bends along its length. More than one arm 40 may be included in the grip feature 36. The mount 42 may extend from the free end of the arm 40, and may be forked or bifurcated to receive the washer 14 within the fork. In the example shown, the mount 42 lies in a plane which is approximately perpendicular to a center longitudinal axis of the cannula 26, although angles greater than or less than 90 degrees are contemplated. The mount 42 may be rigidly fixed to the arm 40, flexibly coupled to the arm for resilient deflection, or hinged to the arm for free rotation. The mount 42 may include prongs 44 which mate with corresponding indentations 46 on the periphery of the washer 14. The prongs 44 may slide, spring, snap, roll, or plunge into the indentations 46. The mount 42 itself may flex or articulate to enable the prongs 44 to engage the indentations 46. Other interconnections are contemplated, such as a skewer mount which spikes into the washer 14.

A method of using the screw 12, washer 14, and cannula 26 will now be described in the context of a facet joint fusion procedure. The washer 14 may be inserted into the mount 42 so that the prongs 44 engage the indentations 46 to hold the washer securely in the mount. The cannula may be positioned with the distal portion 30 resting against the inferior articular process 2 of the superior vertebra and the washer 14 and mount 42 within the joint space between the inferior articular process 2 and the superior articular process 4 of the inferior vertebra. The torque transmission feature 20 of the screw 12 may be coupled to a screw driver (not shown). The screw 12 and screw driver may be advanced through the aperture 34 of the cannula 26 until the distal shaft 18 of the screw rests against the inferior articular process 2. The screw 12 may be driven through the inferior articular process 2, through the aperture 24 of the washer 14, and through the superior articular process 4. Optional additional steps may include placing a guide wire through the cannula, articular processes 2, 4, and aperture 24 to establish a trajectory for the screw 12 to follow; drilling a pilot hole for the screw 12 through the inferior articular process 2 and/or the superior articular process 4; tapping a hole for the screw 12 through the inferior articular process 2 and/or the superior articular process 4; or using medical imaging to verify instrument and/or implant position.

Referring to FIG. 5, the facet washer fixation system 10 may include a rasp 48. The rasp 48 may include a proximal portion 50 and a distal portion 52. The proximal portion 50 may include an elongated shaft 54. A grip feature (not shown) may be present on the proximal portion 50. The distal portion 52 may include an arm 56 which carries a rasp head 58 in a particular orientation and at a particular distance from the distal portion 52 of the rasp 48. The rasp head orientation and distance may be comparable to those for the mount 42. The arm 56 may extend longitudinally from the distal portion 52. The arm 56 may extend from one side of the distal portion 52, and may include one or more bends along its length. More than one arm 56 may be included. The rasp head 58 may extend from the free end of the arm 56. In the example shown, the rasp head 58 lies in a plane which is approximately perpendicular to a center longitudinal axis of the shaft 54, although angles greater than or less than 90 degrees are contemplated. The rasp head 58 may be rigidly fixed to the arm 56, flexibly coupled for resilient deflection, or hinged for free rotation. The rasp head 58 may be generally disc shaped, curved, polygonal, asymmetric, or irregular, and may include cutting features 60 on at least one surface. The cutting features may be blades, teeth, ridges, serrations, points, or other projecting asperities. The cutting features may instead be grooves, channels, or declivities. The rasp head 58 may be a hollow grater structure. The distal portion 52 may resemble the washer holding feature 38 of the cannula 26.

A method of using the rasp 48 will now be described in the context of the facet joint fusion procedure described above. The rasp 48 may be positioned with the rasp head 58 within the joint space between the inferior articular process 2 and the superior articular process 4. The rasp 48 may be manipulated to move the rasp head 58 against one or both articular surfaces to roughen or remove articular cartilage, subchondral bone, and the like to prepare a space to receive the washer 14. The rasp head 58 may be moved in a plane generally parallel to the articulating surfaces, although movement in other directions is contemplated. The rasp head motion may be reciprocating, oscillating, circular, oval, elliptical, figure-eight, or irregular. The rasp 48 may be in the cannula aperture 34 during use. A set or kit of variously sized and shaped rasps or rasp heads may be provided. The rasp or rasp head may be replaceable and/or disposable.

Referring to FIG. 6, a polyaxial taper lock screw and plate system 70 may include a washer 72, a taper component 74, a plate 76, a pad 78, and a fastener 80.

The washer 72 may be a generally annular component with a plate-facing surface 82, or obverse, and an opposite reverse surface 84. A threaded hole 86 may extend through the washer between the obverse and reverse surfaces 82, 84. The plate-facing surface 82 may include an indentation 88 or concavity around the hole 86. The reverse surface 84 may be convex. The washer may include a torque transmission feature (not shown). For example, a hex key may be formed in an outer periphery of the washer.

The taper component 74 may include a round, generally tubular body 90 with a flange 92 at one end and a full length central longitudinal hole 94. The flange 92 may be at least partially received within the indentation 88 of the washer 72.

The plate 76 may include a bone-facing surface 94, or obverse, and an opposite reverse surface 96. A hole 98 may extend through the plate 76 between the obverse and reverse surfaces 94, 96. The hole 98 may receive the body 90 of the taper component 74 with clearance, line to line fit, interference fit, or taper fit. The bone-facing surface 94 may include an indentation 100 around the hole 98. The indentation 100 may be spherical, conical, parabolic, elliptical, asymmetric, or irregular. The plate 76 may include a rim 102, or lip, that encircles the indentation 100. The internal diameter of the indentation 100 may be larger than the internal diameter of the rim 102, so that the rim 102 forms a constriction around the indentation 100.

The pad 78 may be described as a polyaxial foot. The pad 78 may include a spherical plate-facing surface 104 and an opposite bone-facing surface 106. The spherical plate-facing surface 104 may fit within the indentation 100 with clearance, line to line fit, or interference fit. The spherical surface 104 may have an external diameter that is larger than the internal diameter of the rim 102, so that the pad 78 is retained with the plate 76 after initial assembly of the pad 78 to the plate 76. The bone-facing surface 106 may include one or more spikes 108. The pad 78 may include a central hole 110. In the example of FIG. 6, the hole 110 may extend perpendicular to the bone-facing surface 106. In other examples, the hole 110 may extend at an acute angle to the bone-facing surface 106. The hole 110 may receive a portion of the body 90 of the taper component 74 with clearance, line to line fit, interference fit, or taper fit. Alternately, the hole 110 may be the same size as the hole 94 in the taper component 74, in which case, the taper component 74 may be integrally formed with the pad 78. The pad 78 may share some or all of the characteristics of the pad 106 disclosed in U.S. patent application Ser. Nos. 12/853,689 and 13/188,325, which are incorporated by reference herein in their entirety.

The fastener 80 may include a proximal head portion 112 and a distal shaft 114. The proximal head portion 112 may be threaded, and may include a torque transmission feature 116. The distal shaft 114 may include a threaded portion 118 to thread into bone. The fastener 80 may include an unthreaded shank portion 120 between the head portion 112 and the threaded portion 118. The shank portion 120 may fit within the hole 110 of the pad 78 and/or the hole 94 of the taper component 74 with clearance, line to line fit, or interference fit. The proximal head portion 112 may thread together with the threaded hole 86 of the washer 72. The threaded portion 118 of the distal shaft 114 may thread into bone.

The polyaxial taper lock screw and plate system 70 may be assembled by forcing the spherical surface 104 of the pad 78 past the rim 102 and into the indentation 100 of the plate 76, after which the pad remains captive to the plate; receiving the body 90 of the taper component 74 in the hole 98 of the plate, with the flange 92 adjacent to the reverse surface 96 of the plate; coupling the taper component to the pad, with the hole 94 of the taper component coaxial with the hole 110 of the pad and the bone-facing surface 106 of the pad faces outward from the indentation 100; receiving the head portion 112 and shank portion 120 of the fastener 80 through the holes 94, 110 so that the distal threaded portion 118 of the fastener extends outwardly from the bone-facing surface 106 of the pad; and threading the proximal head portion of the fastener into the threaded hole of the washer 72, with the obverse of the washer facing the plate. At first, the fastener 80 and washer 72 may be threaded together with fingertips. The fastener, polyaxial pad 78, and taper component 74 may polyaxially pivot as a unit about the center of the spherical surface 104 within the indentation 100. As the fastener and washer are threaded together, the fastener, polyaxial pad 78, and taper component 74 may be drawn as a unit toward the washer until the polyaxial pad binds within the indentation 100 to lock the system 70 components rigidly together.

In one method of use, the washer 72, taper component 74, plate 76, pad 78, and fastener 80 may be pre-assembled but not locked together. A first tool (not shown) may engage the torque transmission feature 116 of the fastener 80, a second tool (not shown) may engage the torque transmission feature of the washer 72, and a third tool (not shown) may stabilize the plate 76. The three tools may nest, although this is not essential. In one example of a nested arrangement, the first tool is a hex driver which is received within the second tool, which is a hex socket. The second tool is received within the third tool, which is a tube terminating in a fork that fits over the width of the plate 76. The first and second tools may be operated together to turn, or drive, the fastener 80 and washer 72 together to thread the fastener 80 into a bone without locking the system 70 components together. During this step, the bone-facing surface 106 of the pad 72 is brought into contact with the bone and the spikes 108 may penetrate the surface of the bone. The first tool may then be held in a fixed position while the second tool is operated to drive the washer 72 relative to the fastener 80 to lock the system 70 components together. During both steps, the third tool may hold the plate 76 in a fixed position. Tools which hold components in a fixed position while torque is applied elsewhere in the system 70 may be referred to as counter torque tools.

In another method of use, the fastener 80 alone may be driven into bone, after which the pad 78, plate 76, taper component 74, and washer 72 may be assembled to the installed fastener 80. The washer 72 may be driven relative to the fastener 80 to lock the system 70 components together as described above.

While the foregoing description describes a single instance of a fastener, pad, taper component, and washer assembled to a plate, multiple instances of these components are contemplated. For example, a plate may include two instances of the described components, such as one instance at each end of the plate. Additional intermediate instances may also be provided. The instances may lie along a straight line, or along any other geometric construct, or they may be randomly positioned on the plate.

Figure 7:
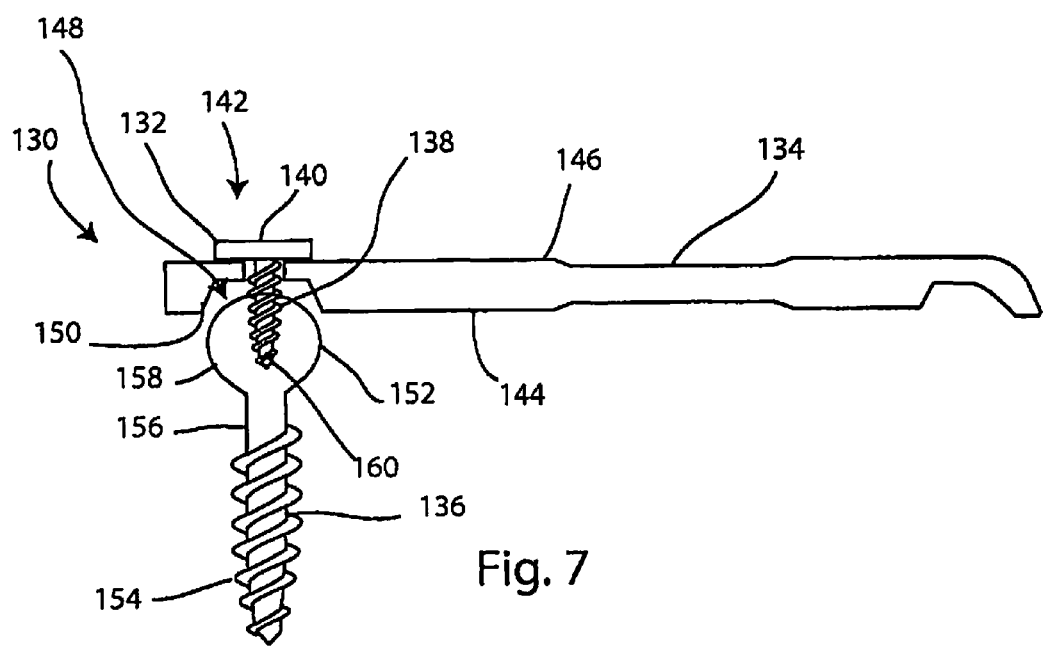
FIG. 7 is a longitudinal cross sectional view of another polyaxial taper lock screw and plate system, taken along a center longitudinal axis of a screw of the system.

Referring to FIG. 7, another polyaxial taper lock screw and plate system 130 may include a taper component 132, a plate 134, and a fastener 136.

The taper component 132 may include a threaded shaft 138 with a flange 140 at one end. The flange 140 may include a torque transmission feature 142, such as a perimeter hex key, central hex socket, slot, or the like.

The plate 134 may include a bone-facing surface 144, or obverse, and an opposite reverse surface 146. A hole 148 may extend through the plate 134 between the obverse and reverse surfaces 144, 146. The hole 148 may receive the shaft 138 of the taper component 132 with clearance, line to line fit, interference fit, or taper fit. The bone-facing surface 144 may include an indentation 150 around the hole 148. The indentation 150 may be spherical, conical, parabolic, elliptical, asymmetric, or irregular. In this example, the indentation 150 is a frustoconical socket. The plate 134 is shown to have two instances of the hole 148 and indentation 150, one at each end of the plate.

The fastener 136 may include a proximal head portion 152, a distal threaded shaft 154, and an unthreaded shank 156 between the head portion 152 and the threaded shaft 154. The head portion 152 may have a spherical outer surface 158 and a central threaded hole 160. The spherical outer surface 158 may be at least partially received in the indentation 150. The threaded hole 160 may thread onto the threaded shaft 138 of the taper component 132.

The polyaxial taper lock screw and plate system 130 may be assembled by seating the head portion 152 of the fastener 136 in the indentation 150 with the distal threaded shaft 154 extending outwardly from the obverse 144 of the plate 134 and threading the shaft 138 of the taper component 132 into the threaded hole 160. At first, the fastener 136 and taper component 132 may be threaded together with fingertips. The fastener 136 and taper component 132 may polyaxially pivot as a unit about the center of the spherical surface 158 within the indentation 150. As the fastener 136 and taper component 132 are threaded together, the fastener and taper component may be drawn toward the plate 134 until the spherical surface 158 binds within the indentation 150 to lock the system 130 components rigidly together.

Referring to FIG. 8, a modular spinous process clamp system 170 may include two plates 172, 174, a plurality of pads 176, a locking mechanism 178, and a sleeve 180, or spacer. Plate 172 may be a first plate and plate 174 may be a second plate. The locking mechanism 178 may include a post 182, a collet 184, and a ring 186.

At least some of the components of system 170 may share characteristics of corresponding components disclosed in spinal fusion implant 100 of U.S. patent application Ser. Nos. 12/853,689 and 13/188,325. However, at least the following characteristics may differ from those disclosed in U.S. patent application Ser. Nos. 12/853,689 and 13/188,325.

The plate 172 may include a spherical or conical socket 188. The post 182 may include a complementary spherical enlargement 190, or head, which fits into the socket 188 to form a polyaxial joint. However, a rigid plate-to-post interconnection may be substituted for the polyaxial joint in some examples.

The plate 174 may lack extension walls.

The sleeve 180 may at least partially encircle the post 182 and may be between the plates 172, 174 when the system 170 is operatively assembled. The sleeve 180 may be an annular or tubular structure with a central longitudinal through hole 192 and an outer surface 194. The sleeve 180 may be made from bone, ceramic, mineral, plastic, metal, glass, elastomer, or other biocompatible materials.

Referring to FIG. 9, another sleeve 200 may have a central longitudinal hole 192 and an outer surface 202 with a larger outer diameter at each end and a smaller outer diameter in the middle. This sleeve 200 may be described as having a waist or an hourglass figure, particularly when viewed in a longitudinal cross section. This sleeve 200 may also be described as having a concave outer profile when viewed in a longitudinal cross section through the center axis of the hole 192.

Referring to FIG. 10, sleeve 180 may have a substantially annular transverse cross section.

Referring to FIG. 11, yet another sleeve 210 may have a central longitudinal hole 192 and a polygonal transverse cross section which is generally centered about the hole 192. Sleeve 210 is shown with a parallelogram cross section, but other shapes are contemplated.

Referring to FIG. 12, yet another sleeve 220 may have a central longitudinal hole 192 and a polygonal transverse cross section which is asymmetrically disposed about the hole 192. A polygonal cross section, such as the illustrated parallelograms of sleeves 210, 220, may complement the shape of an interspinous process gap.

Referring to FIG. 13, yet another sleeve 230 may have a central longitudinal hole 192 and an H-shaped longitudinal cross section. Sleeve 230 may also resemble a spool. Sleeve 230 may include enlarged flanges 232, 234, or rims, at each end and a reduced diameter midsection 236. Sleeve 230 may be described as having a concave outer profile in longitudinal cross section.

Any of the sleeves 200, 210, 220, 230 may take the place of sleeve 180 in the system 170. A kit of sleeves may be provided. The kit may contain several sleeve morphologies, and several sizes in each morphology.

Referring to FIGS. 14-15, another spinous process clamp system 250 may include curved plates 252, 254 which may complement a spinal lordotic or kyphotic curve. The plates 252, 254 may include slots 256, or other arcuate guides such as grooves or rails, to permit longitudinal adjustment of pads 258, locking mechanism 260, or both. The system 250 may also include additional grips 262 between the plates 252, 254. While FIG. 15 shows two opposing grips 262 with the locking mechanism 260, the grips 262 may be any number, and may be positioned anywhere between the plates. The grips may be static or movable relative to the plates 262, 264.

Figure 16:
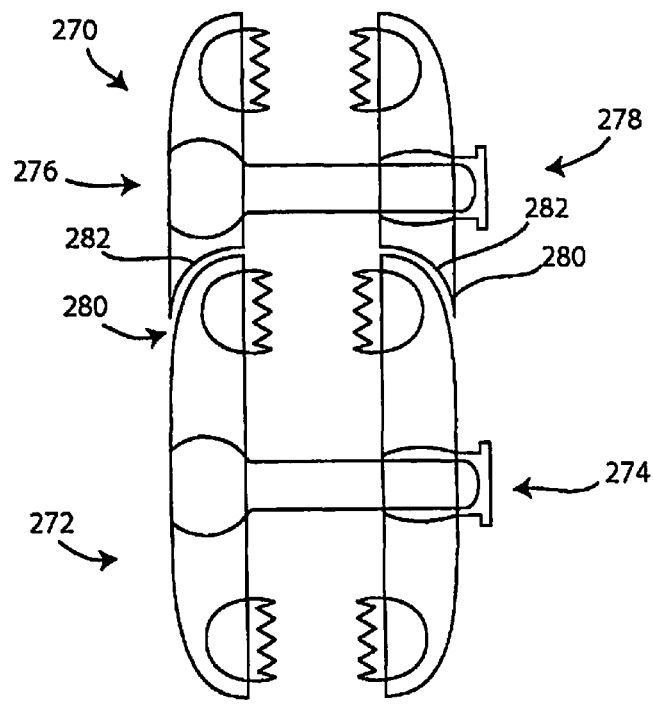
FIG. 16 is a top cross sectional view of a multi-level bone plate system.
Figure 17:
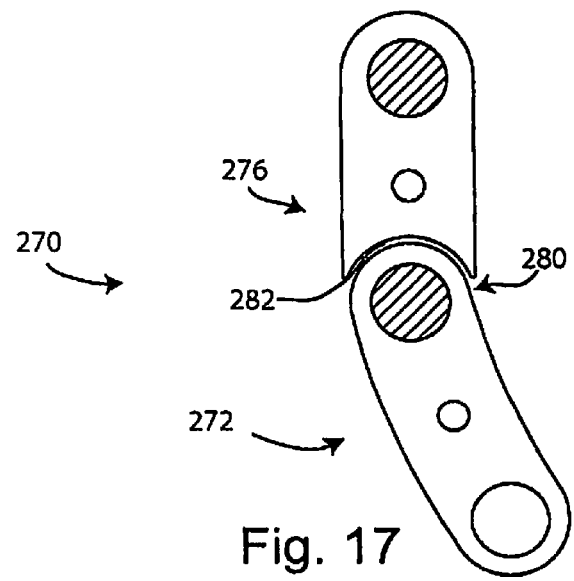
FIG. 17 is a side cross sectional view of the system of FIG. 16.

Referring to FIGS. 16-17, a multi-level bone plate system 270 may include a primary system 272 with a first locking mechanism 274, and an augmentation system 276 with a second locking mechanism 278. A locking mechanism 280 on each side of the construct links the primary and augmentation plates together. The locking mechanism 280 may include an arcuate or spherical mechanically locking interface 282. While FIGS. 16-17 show one augmentation system 276, other examples of this technology may include more augmentation systems mechanically linked in daisy chain fashion to address any number of spinal levels. Yet other examples may include augmentation systems linked to each end of the primary system 272.

Referring to FIG. 18, an expandable interspinous plate system 300 may include plates 302, 304, pads 306, a locking mechanism 308, and a cage 310. The locking mechanism may include a post 312, a collet 314, and a ring 316.

The cage 310 may occupy a position around the post 312 and between the plates 302, 304 when the system 300 is operatively assembled. The cage 310 may reside in an interspinous process space when implanted as part of the system 300. Referring to FIG. 19, the cage 310 may be divided into two portions 318, 320 which nest, or telescope, so that a width 322 of the cage may be increased or decreased as desired. In this arrangement, the cage 310 can adjust parallel to the post to fit precisely between plates 302, 304, and it may provide good exposure for loading materials into the cage. The cage 310 may be said to reversibly expand and contract. Each portion 318, 320 may have a square channel shape. Nesting may be accomplished by making one channel narrower than the other so that the narrow channel is received within the wider channel, or by staggering two identical channels. Each end of each channel may be open or closed. The portions 318, 320 include slots 324, 326, or openings, sized to accept the post 312. The slots 324, 326 may permit the cage 310 to pivot around the post 312, therefore the cage 310 may assume an angled orientation relative to one or both of the plates 302, 304.

Referring to FIG. 20, another cage 330 may present an overall trapezoidal shape when its two portions 332, 334 are nested. A first width 336 may be greater than an opposite second width 338 of the trapezoid.

Referring to FIG. 21, yet another cage 340 illustrates a narrow channel portion 342 nesting inside a wide channel portion 344.

Any of the cages 310, 330, 340 may enclose or support a bone graft, a scaffold for bone growth, or the like. The enclosed material may be a solid block or morselized pieces. Cages may be fenestrated or otherwise open to provide pathways for a bone fusion mass to develop. Cages may be load-bearing or load-sharing with the rest of the system 300. For example, the cages may be open at cephalad and caudal faces for spinal fusions.

Referring to FIG. 22, another expandable interspinous plate system 360 may include a cage 370 which is adjustable in a direction generally parallel to the plates 362, 364, or generally perpendicular to the post. The cage 370 may include two portions 372, 374 which nest or telescope so that a length 376 of the cage 370 may be adjusted as desired. The two portions 372, 374 may be square channels, and may include open ended slots 378, 380 which accept a post 382 and enable the cage 370 to pivot around the post 382. The cage 370 may be rotated to an orientation in which the adjustment direction is substantially parallel to a physiologic load direction, which may subject a contained graft to compressive and/or tensile loads after implantation. Cage 370 may be fenestrated or otherwise open to provide pathways for a bone fusion mass to develop.

Referring to FIG. 24, another cage 390 may include at least a partial anterior wall 392 on one or both portions 394, 396.

Referring to FIG. 25, system 360 is shown implanted adjacent to spinous processes 384, 386. It can be seen that cage 370 rests between the spinous processes and at an acute angle relative to plate 362.

Figure 26:
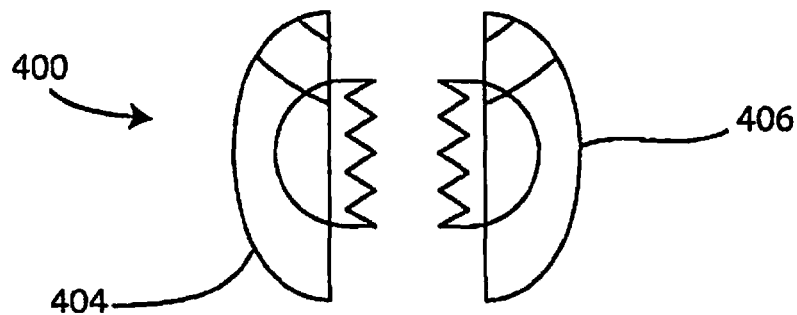
FIG. 26 is an end view of yet another bone plate system.
Figure 27:
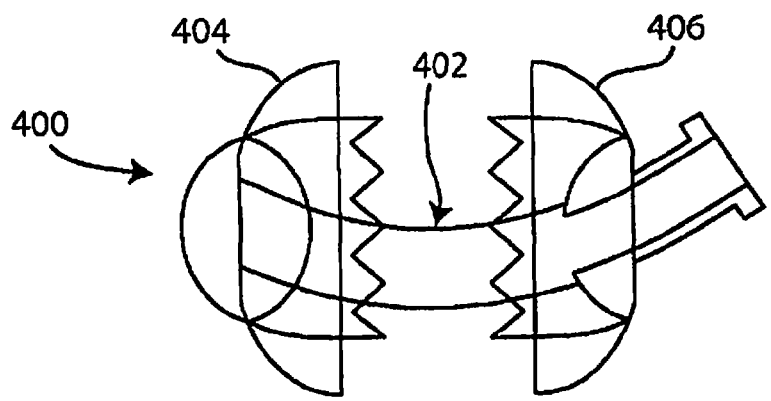
FIG. 27 is a transverse cross sectional view of the bone plate system of FIG. 26.
Figure 28:
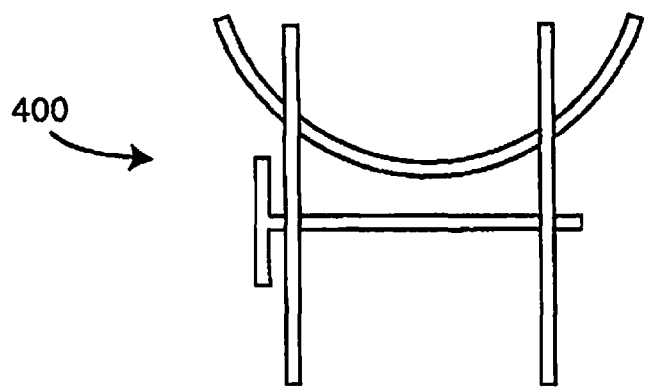
FIG. 28 is a top view of the bone plate system of FIG. 26.
Figure 29:
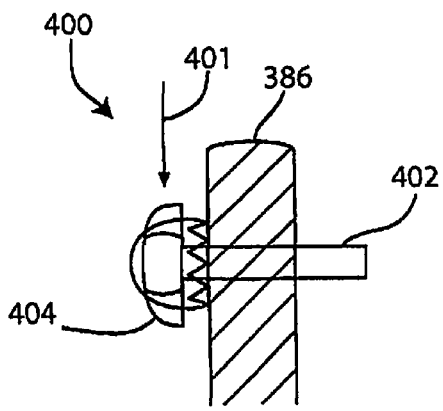
FIG. 29 is a transverse cross sectional view of the bone plate system of FIG. 26 after introduction of a plate and a post to a surgical site.
Figure 30:
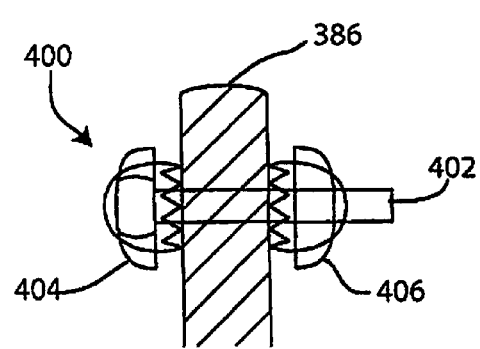
FIG. 30 is a transverse cross sectional view of the bone plate system of FIG. 26 after introduction of another plate and locking components to the surgical site.
Figure 31:
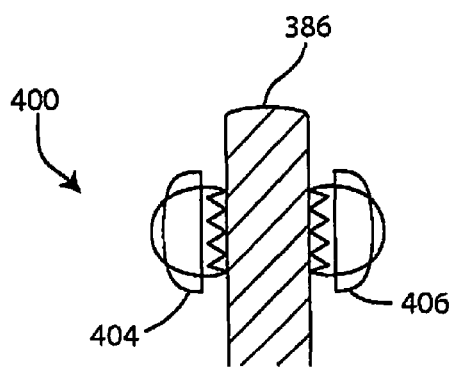
FIG. 31 is a transverse cross sectional view of the bone plate system of FIG. 26 after final locking.

Referring to FIGS. 26-28, a minimally invasive bone plate system 400 may include a curved post 402, which may facilitate insertion of the post after placement of plates 404, 406. FIGS. 29-31 illustrate three steps in an example method of use. In FIG. 29, plate 404 and post 402 may be inserted as a unit on one side of a series of spinous processes 384, 386, along direction arrow 401. In FIG. 30, plate 406 is attached over post 402 on the other side of the spinous processes. In FIG. 31, the system 400 has been fully locked together around the spinous processes.

Figure 32:
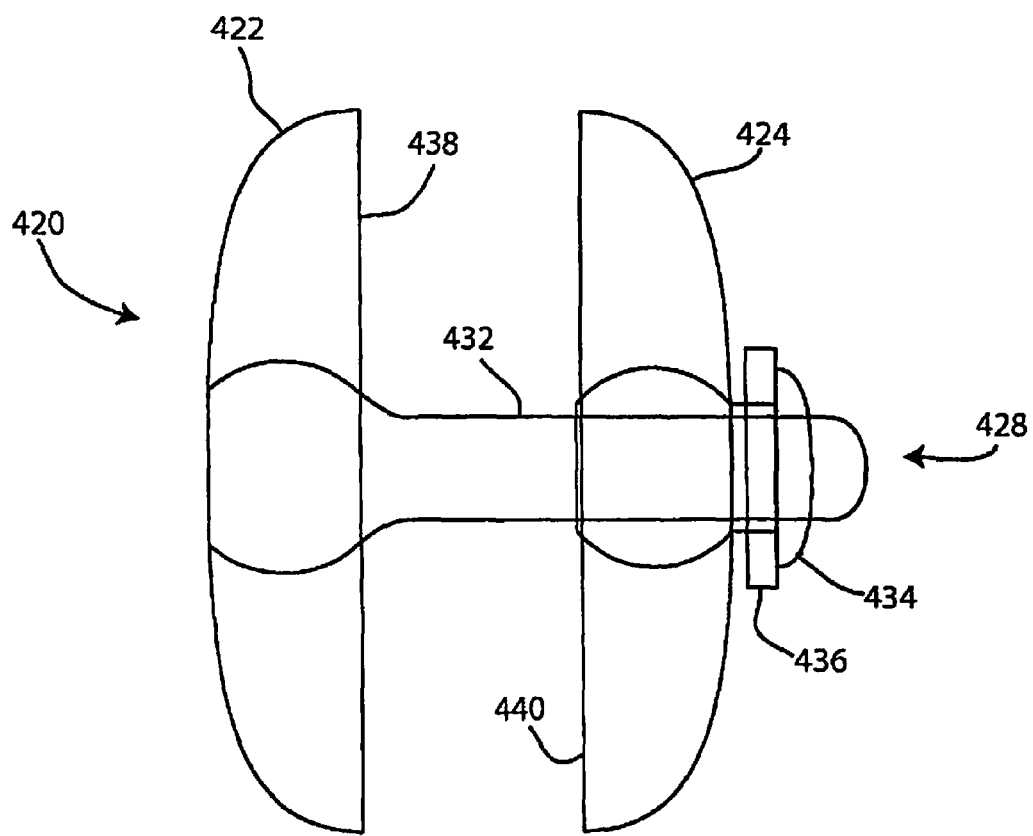
FIG. 32 is a top cross sectional view of an interspinous process system.

Referring to FIG. 32, an extension limiting interspinous process spacer system 420 may include plates 422, 424 and locking mechanism 428. The locking mechanism 428 may include a post 432, a collet 434, and a ring 436. Each plate 422, 424 may couple to the locking mechanism 428 at a polyaxial joint. The plates 422, 424 may have smooth bone-facing or obverse sides 438, 440 to permit the adjacent spinous processes to separate during spinal flexion. Spinal extension may be limited by the outside diameter of the post 432.

Figure 33:
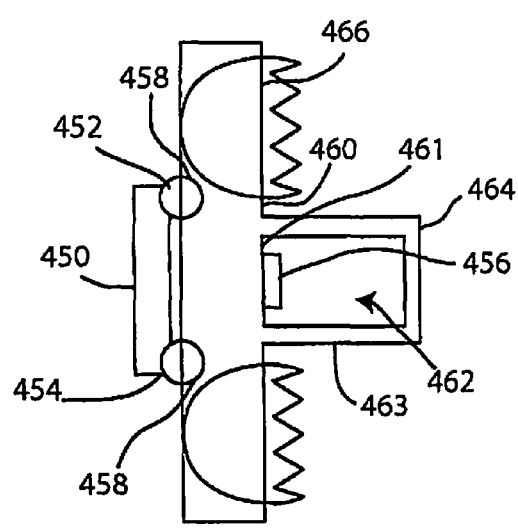
FIG. 33 is a top view of an extension plate coupled to an instrument.

Referring to FIG. 33, an instrument 450 provides three-point positive locking to an extension plate 460. The instrument 450 includes two lateral connections 452, 454 and a medial connection 456. More specifically, the instrument may engage lateral cups 458, or sockets, and a medial inner lip 461, or edge, of a window 462 in an extension wall 464. The lateral cups 458 may share some or all of the characteristics of the instrument connection feature 150 disclosed in U.S. patent application Ser. Nos. 12/853,689 and 13/188,325.

Figure 34:
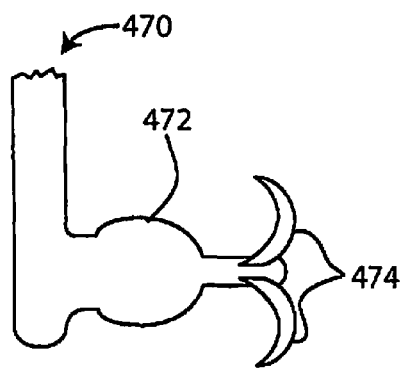
FIG. 34 is a side view of another instrument.
Figure 35:
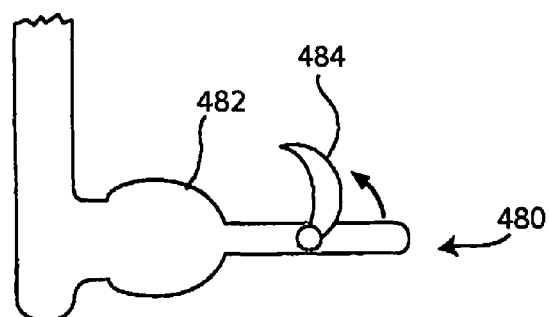
FIG. 35 is a side view of yet another instrument.

Referring to FIGS. 34-35, instruments 470, 480 include positive locking through the lateral cups 458. Instrument 470 includes an enlarged tip 472 which is received in the lateral cup 458. Protruding from the tip 472 are forked tongues 474 which may be stored in a retracted position within the tip 472 or deployed to an extended flared position outside the tip. When the tip 472 is in the lateral cup 458, the tongues 474 may be extended through the lateral cup to grapple with the obverse surface 466 of the plate 460. Instrument 480 includes an enlarged tip 482 with a protruding deployable lever 484 that also grapples with the obverse 466 of the plate 460.

Figure 36:
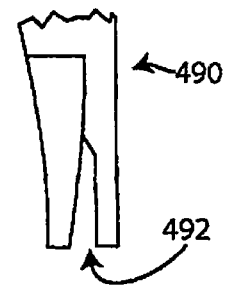
FIG. 36 is a side view of yet another instrument.

Referring to FIG. 36, instrument 490 includes a fork 492 which grips an exposed lip 463 of the window 462.

Figure 37:
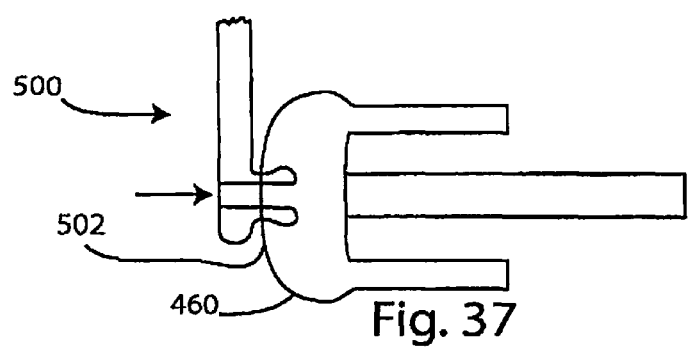
FIG. 37 is an end view of an extension plate coupled to yet another instrument.
Figure 45:
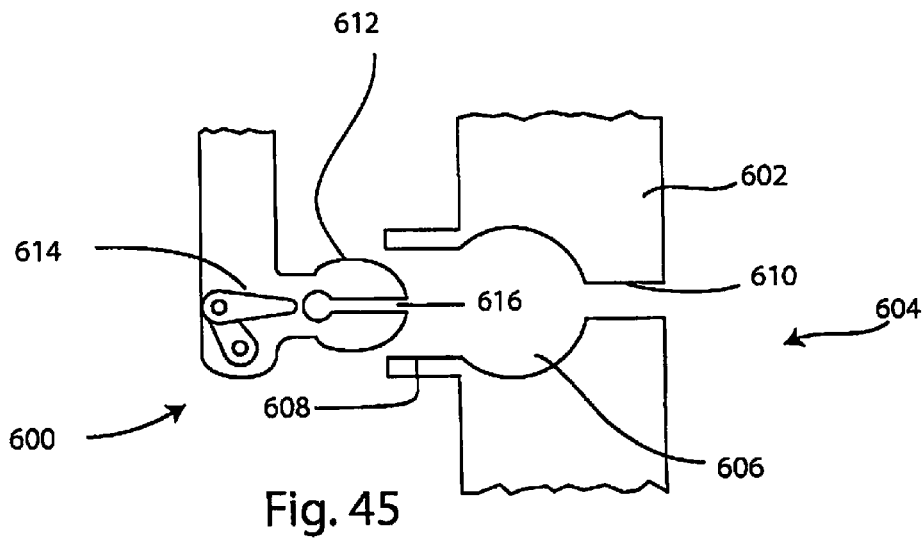
FIG. 45 is a cross sectional detail view of a plate and an instrument.

Referring to FIG. 37, instrument 500 includes a spherical expanding tip 502 which is received in the lateral cup 458. The tip 502 expands when a shaft is driven through the tip 502 along its length. The tip 502 may be described as an expanding collet. FIG. 45 shows another example of an instrument 600 with a similar structure and function.

Figure 38:
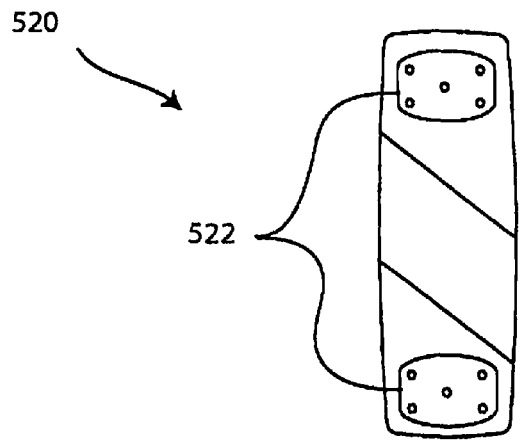
FIG. 38 is a side view of a plate with non-spherical pads.

Referring to FIG. 38, a bone plate system 520 may include non-spherical or non-circular swiveling grips 522, or pads. The range of motion of the non-spherical grips 522 may be selectively limited by the grip geometry.

Figure 39:
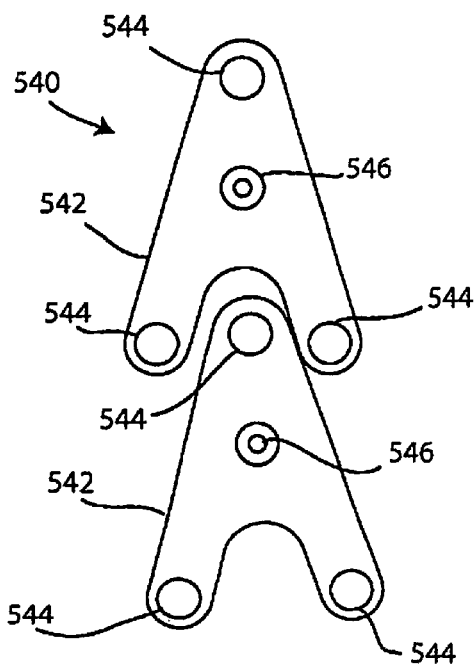
FIG. 39 is a side view of a segmental multi-level spinous process plating system.

Referring to FIG. 39, another multi-level bone plate system 540 may include chevron shaped plates 542. Each plate 542 may include three pads 544 arranged in a triangle pattern complementary to the chevron shape. Each plate may also include a locking mechanism 546. Consecutive plates 542 nest together as shown so that two plates may be secured to a single spinous process. The nesting shapes have sufficient clearance to permit angulation of consecutive plates to adapt to spinal lordotic, kyphotic, or scoliotic curves.

Figure 40:
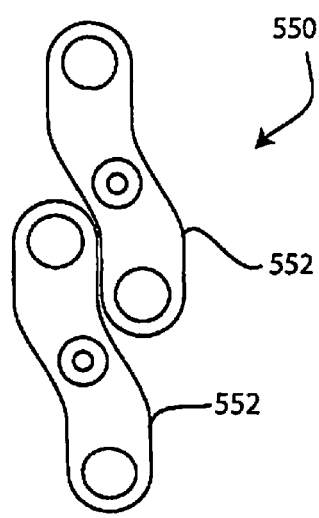
FIG. 40 is a side view of another segmental multi-level spinous process plating system.

Referring to FIG. 40, yet another segmental multi-level bone plate system 550 includes S-bend plates 552. Consecutive plates partially bypass each other so that two plates may be secured to a single spinous process. Although only two consecutive plates are shown in FIGS. 39-40, more plates may be included depending on the number of spinal levels to be treated.

Referring to FIGS. 41-42, another bone plate system 560 includes a plate 562 with an elongated slot 564 which receives the locking mechanism 566. In this arrangement, a polyaxial washer 568 may support a collet 570 in the slot 564 so that the locking mechanism 566 may be positioned as desired along the slot.

Referring to FIG. 43, another plate 580 for segmental multi-level fixation may have a generally T-shaped profile. Pads (not shown) may be located in the ends of the crossbar of the T so that two plates may be anchored to each spinous process.

Referring to FIG. 44, another cage 590 is shown. The cage 590 may be a box shape with four pillars 592 supporting two walls 594. A hole 596 extends through both walls. Windows 598 are defined between the pillars. The hole 596 may receive a post of a locking mechanism, and the cage 590 may rest between two plates in an operative assembly. This cage may contain or support bone graft or other materials, such as osteogenic materials, within the box.

Referring to FIG. 45, a transverse cross sectional exploded view shows an instrument 600 and a portion of a plate 602.

Plate 602 includes an instrument connection feature 604, which has an enlarged middle portion 606 between a first portion 608 and a second portion 610.

Instrument 600 includes an enlarged tip 612 and a plunger 614. The enlarged tip 612 is received in the middle portion 606 of the instrument connection feature 604. The tip 612 is hollow and includes at least one slit 616 to impart flexibility to the tip. In an extended position, the plunger 614 is received in the tip 612 and forces the tip to spread apart or enlarge for a tight fit in the middle portion 606 of the instrument connection feature 604. The plunger 614 is actuated by an arm 618 which is coupled to a control (not shown). The plunger 614 moves between a disengaged or retracted position and an engaged, or extended position in response to the control.

Figure 46:
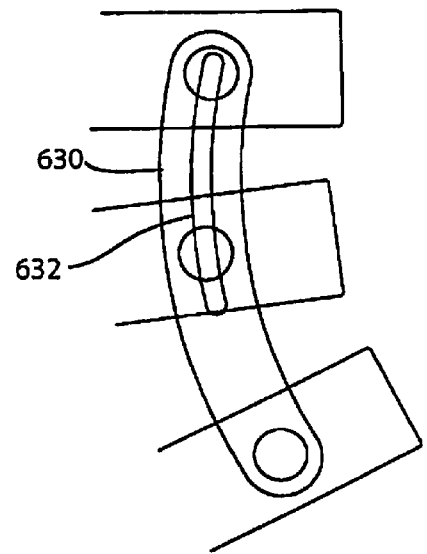
FIG. 46 is a side view of another bone plate system.
Figure 47:
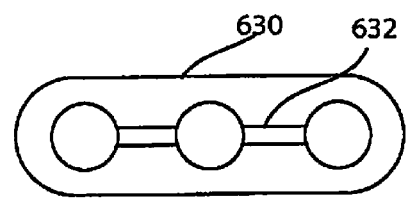
FIG. 47 is another side view of the bone plate system of FIG. 46.
Figure 48:
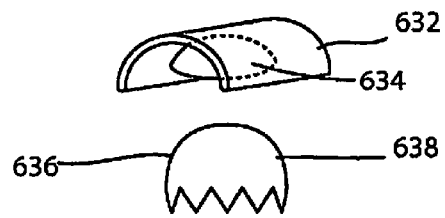
FIG. 48 is an exploded view of portions of the system of FIG. 46.

Referring to FIGS. 46-48, another curved plate 630 includes a curved trough 632. The trough may receive one or more pads 636 which may be movably mounted in the trough. For example, the trough 632 may include a spherical cup 634 for engagement with the pad 636. In another example, a spherical surface 638 of the pad 636 may be directly retained and slidable in the trough 632.

Referring to FIG. 49, a plate compressor 650 may include opposing jaws 652, 654, a main pivot 656, opposing handles 658, 660, and an optional ratchet mechanism 662. The plate compressor 650 may connect to the plates of any of the spinous process systems disclosed herein, and may urge the plates together and automatically maintain a compressive force between the plates until the ratchet bar 662 is released.

Referring to FIGS. 50 and 52-53, a provisional locking arm 670 may include a jaw 672, a main pivot receiver 674, and a handle 676. The provisional locking arm 670 may be added to the plate compressor 650 by hooking the main pivot receiver 674 onto the main pivot 656. The jaw 672 terminates in a collet fork 678 which isolates the applied force to push a collet component of a plate locking mechanism toward the plates for provisional locking. The provisional locking arm 670 may include a force indicator 680 which signals when a provisional locking force threshold has been reached. The force indicator 680 may be a beam. The signal provided by the force indicator may be visual, auditory, tactile, or any combination. The signal may be produced by differential deflection between the handle 676 and the force indicator 680.

Referring to FIG. 51, a final locking arm 690 may include a jaw 692, a main pivot receiver 694, and a handle 696. The final locking arm 690 may be added to the plate compressor 650 by hooking the main pivot receiver 694 onto the main pivot 656, regardless of the presence or absence of the provisional locking arm 670 on the compressor 650. The jaw 692 terminates in a ring 698 which isolates its applied force to push a ring component of a plate locking mechanism toward the plates for final locking. The final locking arm 690 may include another force indicator 700 calibrated for a final locking force threshold.

When the provisional locking arm 670 and final locking arm 690 are coupled to the plate compressor 650, the combination may have many of the characteristics set forth for the instrument 350 disclosed in U.S. patent application Ser. No. 13/188,325.

The components of the systems disclosed herein are preferably formed of titanium or titanium alloy. In other embodiments, component parts may comprise cobalt-chrome and its alloys, stainless-steel, titanium and its alloys, titanium carbide, titanium nitride, ion-implantation of titanium, diffusion hardened metals, diamond like coatings, diamond-like carbon, zirconium nitride, niobium, oxinium or oxidized zirconium, ceramics such as alumina and zirconia, polymers, or other biocompatible materials. Any part may comprise a combination of any of the materials listed, and the systems may comprise parts made of differing materials.

Any of the components disclosed herein may include surface treatments or additives in one or more of the component materials to provide beneficial effects such as anti-microbial, analgesic or anti-inflammatory properties. Any of the components disclosed herein may include coatings or treatments to provide surface roughening, including but not limited to knurling or porous coating, among others. Such treatments may be directionally applied to promote movement between component parts in one direction, and/or increase friction between component parts in another direction.

The present invention may be embodied in other specific forms without departing from its spirit or essential characteristics. It is appreciated that various features of the above described examples and embodiments may be mixed and matched to form a variety of other combinations and alternatives. It is also appreciated that this system should not be limited simply to facet joint fixation. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A bone plate assembly, comprising:
a first plate having a proximal and a distal end, the first plate further comprising an obverse side and a reverse side opposite the obverse side;
a second plate having a proximal and a distal end, the second plate further comprising an obverse side and a reverse side opposite the obverse side;
a locking mechanism disposed between the first and second plates, said locking mechanism defining a longitudinal axis, wherein the locking mechanism comprises a first portion associated with the first plate and a second portion associated with the second plate;
a first gripping pad configured to recess within the obverse side at the proximal end of the first plate and comprising a face including a plurality of protrusions configured to contact a bone and a first pad pivot element, wherein the first pad pivot element is configured to allow the first gripping pad to pivot about at least one axis relative to the first plate; and
a second gripping pad configured to recess within the obverse side at the proximal end of the second plate and comprising a face including a plurality of protrusions configured to contact a bone and a second pad pivot element, wherein the second pad pivot element is configured to allow the second gripping pad to pivot about at least one axis relative to the second plate.

2. The bone plate assembly of claim 1, wherein the first portion of the locking mechanism engages with the second portion of the locking mechanism to provide an interference lock.

3. The bone plate assembly of claim 1, wherein the first plate is configured to allow the first plate to polyaxially rotate relative to the second plate.

4. The bone plate assembly of claim 1, wherein the first gripping pad pivots relative to the first plate through a range of motion;
wherein the range of motion comprises a neutral position and a tilted position;
wherein the face is parallel to the obverse side of the first plate in the neutral position;
wherein the face is oblique to the obverse side of the first plate in the tilted position.

5. The bone plate assembly of claim 1, wherein, in an initial configuration, the first gripping pad freely rotates relative to the first plate; and
wherein, in a final configuration, the first gripping pad is in a locked position relative to the first plate.

6. A bone plate assembly, comprising:
a first plate comprising a first obverse side and a first reverse side opposite the first obverse side, said first plate comprising at least one pad, said pad including a plurality of protrusions configured to contact a bone surface, said at least one pad of said first plate configured to allow the pad to pivot about at least one axis relative to the first plate;
a second plate comprising a second obverse side and a second reverse side opposite the second obverse side, said second plate comprising at least one pad, said pad including a plurality of protrusions configured to contact a bone surface, said at least one pad of said second plate configured to allow the pad to pivot about at least one axis relative to the second plate; and
a locking mechanism disposed between the first and second plates, said locking mechanism defining a longitudinal axis;
wherein the bone plate assembly has an unlocked configuration and a locked configuration;
wherein the bone plate assembly is configured to transition from the unlocked configuration to the locked configuration in response to a compression force exerted along the longitudinal axis, said compression force urging the first obverse side and the second obverse side together;

wherein the locking mechanism has at least a first portion associated with the first plate and at least a second portion associated with the second plate, wherein the first portion and the second portion are configured to engage one another in the locked configuration.

7. The bone plate assembly of claim 6, wherein the first plate is configured to allow the first plate to polyaxially rotate relative to the second plate in the unlocked configuration.

8. The bone plate assembly of claim 6, wherein the at least one pad of the first plate is configured to pivot relative to the first plate through a range of motion;
wherein the range of motion comprises a neutral position and a tilted position;
wherein the pad is parallel to the obverse side in the neutral position;
wherein the pad is oblique to the obverse side in the tilted position.

9. The bone plate assembly of claim 6, wherein, in an initial configuration, the at least one pad of the first plate is configured to rotate relative to the first plate; and
wherein, in a final configuration, the at least one pad of the first plate is in a locked position relative to the first plate.

10. The bone plate assembly of claim 9, further comprising a spacer, wherein, in the initial configuration, the spacer prevents unintentional locking of the at least one pad of the first plate relative to the first plate; wherein, in the final configuration, the spacer permits intentional locking of the at least one pad of the first plate relative to the first plate.

11. A plate assembly for attachment to a bone surface, comprising:
a first plate comprising a first obverse side and a first reverse side opposite the first obverse side, said first plate comprising at least one pad including a plurality of protrusions configured to contact a bone surface;
a second plate comprising a second obverse side and a second reverse side opposite the second obverse side, said second plate comprising at least one pad including a plurality of protrusions configured to contact a bone surface; and
a locking mechanism coupling the first plate to the second plate so that the first obverse side faces the second obverse side, said locking mechanism disposed between the first obverse side of the first plate and the second obverse side of the second plate;
wherein the plate assembly has an unlocked configuration and a locked configuration;
wherein, in the unlocked configuration, the first plate rotates and translates relative to the second plate and permits alignment of the first plate to the bone surface;
wherein, in the locked configuration, the first plate is rotationally and translationally fixed relative to the second plate;
wherein the plate assembly is configured to transition from the unlocked configuration to the locked configuration in response to a compression force urging the first obverse side and the second obverse side together.

12. The plate assembly of claim 11, wherein the locking mechanism has a first portion and a second portion;
wherein an interference lock is provided by the engagement of the first portion with the second portion.

13. The plate assembly of claim 11, wherein, in the unlocked configuration, the first plate is configured to polyaxially rotate relative to the second plate.

14. The plate assembly of claim 11, wherein, in the unlocked configuration, the first plate is configured to polyaxially rotate relative to the locking mechanism.

15. The plate assembly of claim 11, wherein the at least one pad of the first plate is configured to polyaxially rotate relative to the first plate within a recess of the first plate in an initial configuration.

16. A plate system for attachment to bone, comprising:
a first plate comprising a first obverse side and a first reverse side opposite the first obverse side;
a second plate comprising a second obverse side and a second reverse side opposite the second obverse side; and
a locking mechanism coupling the first plate to the second plate with the first obverse side facing the second obverse side, the locking mechanism between the first and second obverse sides;
wherein the locking mechanism comprises a first portion and a second portion, the first portion associated with the first plate, and the second portion associated with the second plate;
wherein the plate assembly has an unlocked configuration and a locked configuration;
wherein, in the locked configuration, the first and second plates are rotationally fixed relative to each other and the first portion of the locking mechanism and the second portion of the locking mechanism are engaged with one another.

17. The plate system of claim 16, wherein, in the unlocked configuration, the first plate is configured to polyaxially rotate relative to the second plate.

18. The plate assembly of claim 16, wherein, in the unlocked configuration, the first plate is configured to polyaxially rotate relative to the locking mechanism.

19. The plate assembly of claim 16, wherein the first plate comprises at least one pad configured to polyaxially rotate relative to the first plate within a recess of the first plate in an initial configuration.

20. The plate assembly of claim 16, wherein the locking mechanism is a separate component from the first plate and the second plate.

* * * * *